US010660978B2

(12) United States Patent
Armstrong et al.

(10) Patent No.: US 10,660,978 B2
(45) Date of Patent: May 26, 2020

(54) DECREASING MICROORGANISMS IN FLUIDS USING ULTRASONIC WAVE TECHNOLOGIES

(71) Applicant: BAKER HUGHES INCORPORATED, Houston, TX (US)

(72) Inventors: Charles David Armstrong, Tomball, TX (US); Crystal Lee, Houston, TX (US)

(73) Assignee: Baker Hughes, a GE company, LLC, Houston, TX (US)

( * ) Notice: Subject to any disclaimer, the term of this patent is extended or adjusted under 35 U.S.C. 154(b) by 265 days.

(21) Appl. No.: 15/170,238

(22) Filed: Jun. 1, 2016

(65) Prior Publication Data
US 2016/0356122 A1 Dec. 8, 2016

Related U.S. Application Data

(60) Provisional application No. 62/169,819, filed on Jun. 2, 2015.

(51) Int. Cl.
C02F 1/36 (2006.01)
A61L 2/025 (2006.01)

(52) U.S. Cl.
CPC ............... *A61L 2/025* (2013.01); *C02F 1/36* (2013.01); *C02F 2303/04* (2013.01); *C02F 2303/20* (2013.01)

(58) Field of Classification Search
CPC .......... C02F 1/36; C02F 1/46104; C02F 1/42; C02F 1/4604; C02F 1/4693; C02F 2101/10; C02F 2103/005; C02F 2301/066; C02F 2301/106; C02F 2303/04; C02F 2303/08; C02F 2101/30; A61L 2/025; C09K 8/54; E21B 37/00; E21B 28/00; E21B 41/00; B01D 61/58; B01D 61/422
See application file for complete search history.

(56) References Cited

U.S. PATENT DOCUMENTS

| | | | | |
|---|---|---|---|---|
| 5,611,993 A | | 3/1997 | Babaev | |
| 8,318,027 B2* | | 11/2012 | McGuire | C02F 1/004 210/151 |
| 9,023,275 B2* | | 5/2015 | McClung, III | E21B 21/065 422/22 |
| 9,243,477 B2* | | 1/2016 | Solenthaler | E21B 28/00 |
| 2007/0272409 A1* | | 11/2007 | Growcock | C09K 8/516 166/278 |
| 2013/0233796 A1 | | 9/2013 | Rao et al. | |
| 2014/0140893 A1 | | 5/2014 | Kohler | |
| 2014/0148367 A1* | | 5/2014 | McCubbins, Jr. | C09K 8/54 507/117 |
| 2014/0202876 A1 | | 7/2014 | Dionne et al. | |
| 2014/0246371 A1 | | 9/2014 | Cao et al. | |
| 2014/0302168 A1* | | 10/2014 | Perry | A01N 59/00 424/613 |
| 2015/0291454 A1* | | 10/2015 | McGuire | C02F 1/36 210/209 |
| 2016/0333652 A1* | | 11/2016 | Mancosky | A61L 2/02 |

FOREIGN PATENT DOCUMENTS

DE 102011105312 A1 * 12/2012 ............. C02F 1/325

OTHER PUBLICATIONS

Chemat, Farid, et al., "Applications of ultrasound in food technology: Processing, preservation and extraction", Ultrasonics Sonochemistry, 18 (2011) 813-835.

* cited by examiner

Primary Examiner — Cameron J Allen
(74) Attorney, Agent, or Firm — Mossman, Kumar & Tyler, P.C.

(57) ABSTRACT

Microbial growth of at least one microorganism may be decreased, prevented, and/or inhibited in a fluid by providing ultrasonic waves to the fluid. In an optional non-limiting embodiment, an amount of at least one gas may be provided to the fluid for further decreasing the microbial population, preventing microbial growth, and/or inhibiting microbial growth. In another non-limiting embodiment, the fluid may be a downhole fluid, such as but not limited to, drilling fluids, completion fluids, production fluids, injection fluids, stimulation fluids, refinery fluids, servicing fluids, and combinations thereof. Alternatively, the fluid or downhole fluid may have a temperature ranging from about 25 C to about 100 C.

15 Claims, No Drawings

DECREASING MICROORGANISMS IN FLUIDS USING ULTRASONIC WAVE TECHNOLOGIES

TECHNICAL FIELD

The present invention relates to methods of decreasing microbial growth of at least one microorganism in a fluid by providing ultrasonic waves to the fluid, optionally heating the fluid to a pre-determined temperature prior to providing the ultrasonic waves, and/or optionally providing the fluid with an effective amount of a gas at the same time or different time from providing the ultrasonic waves.

BACKGROUND

Microorganisms may be found in various fluids. Such fluids may be downhole fluids, such as drilling fluids, completion fluids, production fluids, injection fluids, stimulation fluids, refinery fluids, servicing fluids, and combinations thereof. Chemical additives, such as polymers and surfactants, may be introduced into the downhole fluids for various reasons that include, but are not limited to, increasing viscosity, increasing the density of the downhole fluid, chemical inhibitors, etc. Chemical compatibility of the downhole fluid with the reservoir formation and formation fluids is key.

Downhole fluids are typically classified according to their base fluid. In water-based fluids, solid particles, such as weighting agents, are suspended in a continuous phase consisting of water or brine. Oil can be emulsified in the water, which is the continuous phase. "Water-based fluid" is used herein to include fluids having an aqueous continuous phase where the aqueous continuous phase can be all water or brine, an oil-in-water emulsion, or an oil-in-brine emulsion.

Brine-based fluids, of course are water-based fluids, in which the aqueous component is brine. Suitable salts for forming the brines include, but are not necessarily limited to, sodium chloride, calcium chloride, zinc chloride, potassium chloride, potassium bromide, sodium bromide, calcium bromide, zinc bromide, sodium formate, potassium formate, ammonium formate, cesium formate, and mixtures thereof.

Oil-based fluids are the opposite or inverse of water-based fluids. "Oil-based fluid" is used herein to include fluids having a non-aqueous continuous phase where the non-aqueous continuous phase is all oil, a non-aqueous fluid, a water-in-oil emulsion, a water-in-non-aqueous emulsion, a brine-in-oil emulsion, or a brine-in-non-aqueous emulsion. In oil-based fluids, solid particles are suspended in a continuous phase consisting of oil or another non-aqueous fluid. Water or brine can be emulsified in the oil; therefore, the oil is the continuous phase. In oil-based fluids, the oil may consist of any oil or water-immiscible fluid that may include, but is not limited to, diesel, mineral oil, esters, refinery cuts and blends, or alpha-olefins. Oil-based fluid as defined herein may also include synthetic-based fluids or muds (SBMs), which are synthetically produced rather than refined from naturally-occurring materials. Synthetic-based fluids often include, but are not necessarily limited to, olefin oligomers of ethylene, esters made from vegetable fatty acids and alcohols, ethers and polyethers made from alcohols and polyalcohols, paraffinic, or aromatic, hydrocarbons alkyl benzenes, terpenes and other natural products and mixtures of these types.

Drilling fluids are used to drill into the subterranean reservoir. Completion fluids may be placed in a well to facilitate final operations prior to initiation of production. Production fluid flows from a formation to the surface of an oil well, such as oil, gas, water, as well as any contaminants (e.g. $H_2S$, asphaltenes, etc.). The consistency and composition of the production fluid may vary.

Refinery fluids are fluids that may be further processed or refined at a refinery. A non-limiting example of a refinery process may include reducing or preventing the formation of foulants. Non-limiting examples of foulants may be or include hydrates, asphaltenes, coke, coke precursors, naphthenates, inorganic solid particles (e.g. sulfates, oxides, scale, and the like), and combinations thereof. Non-limiting examples of fluids to be refined include crude oil, production water, and combinations thereof.

Servicing fluids, such as remediation fluids, stimulation fluids, workover fluids, and the like, have several functions and characteristics necessary for repairing a damaged well. Such fluids may be used for breaking emulsions already formed and for removing formation damage that may have occurred during the drilling, completion and/or production operations. The terms "remedial operations" and "remediate" are defined herein to include a lowering of the viscosity of gel damage and/or the partial or complete removal of damage of any type from a subterranean formation. Similarly, the term "remediation fluid" is defined herein to include any fluid that may be useful in remedial operations. A stimulation fluid may be a treatment fluid prepared to stimulate, restore, or enhance the productivity of a well, such as fracturing fluids and/or matrix stimulation fluids in one non-limiting example.

Hydraulic fracturing is a type of stimulation operation, which uses pump rate and hydraulic pressure to fracture or crack a subterranean formation in a process for improving the recovery of hydrocarbons from the formation. Once the crack or cracks are made, high permeability proppant relative to the formation permeability is pumped into the fracture to prop open the crack. When the applied pump rates and pressures are reduced or removed from the formation, the crack or fracture cannot close or heal completely because the high permeability proppant keeps the crack open. The propped crack or fracture provides a high permeability path connecting the producing wellbore to a larger formation area to enhance the production of hydrocarbons.

The development of suitable fracturing fluids is a complex art because the fluids must simultaneously meet a number of conditions. For example, they must be stable at high temperatures and/or high pump rates and shear rates that can cause the fluids to degrade and prematurely settle out the proppant before the fracturing operation is complete. Various fluids have been developed, but most commercially used fracturing fluids are aqueous based liquids that have either been gelled or foamed to better suspend the proppants within the fluid.

Injection fluids may be used in enhanced oil recovery (EOR) operations, which are sophisticated procedures that use viscous forces and/or interfacial forces to increase the hydrocarbon production, e.g. crude oil, from oil reservoirs. The EOR procedures may be initiated at any time after the primary productive life of an oil reservoir when the oil production begins to decline. The efficiency of EOR operations may depend on reservoir temperature, pressure, depth, net pay, permeability, residual oil and water saturations, porosity, fluid properties, such as oil API gravity and viscosity, and the like.

EOR operations are considered a secondary or tertiary method of hydrocarbon recovery and may be necessary when the primary and/or secondary recovery operation has left behind a substantial quantity of hydrocarbons in the subterranean formation. Primary methods of oil recovery use the natural energy of the reservoir to produce oil or gas and do not require external fluids or heat as a driving energy; EOR methods are used to inject materials into the reservoir that are not normally present in the reservoir.

Secondary EOR methods of oil recovery inject external fluids into the reservoir, such as water and/or gas, to re-pressurize the reservoir and increase the oil displacement. Tertiary EOR methods include the injection of special fluids, such as chemicals, miscible gases and/or thermal energy. The EOR operations follow the primary operations and target the interplay of capillary and viscous forces within the reservoir. For example, in EOR operations, the energy for producing the remaining hydrocarbons from the subterranean formation may be supplied by the injection of fluids into the formation under pressure through one or more injection wells penetrating the formation, whereby the injection fluids drive the hydrocarbons to one or more producing wells penetrating the formation. EOR operations are typically performed by injecting the fluid through the injection well into the subterranean reservoir to restore formation pressure, improve oil displacement or fluid flow in the reservoir, and the like.

Examples of EOR operations include water-based flooding and gas injection methods. Water-based flooding may also be termed 'chemical flooding' if chemicals are added to the water-based injection fluid. Water-based flooding may be or include, polymer flooding, ASP (alkali/surfactant/polymer) flooding, SP (surfactant/polymer) flooding, low salinity water and microbial EOR; gas injection includes immiscible and miscible gas methods, such as carbon dioxide flooding, and the like.

The presence of microorganisms in downhole fluids is undesirable for various reasons. The subterranean reservoirs currently being developed have increased amounts of microorganisms present within the reservoir and thereby contaminate production fluids, as well as any fluids circulated therein (e.g. drilling fluids, completion fluids, etc.). Several microorganisms produce toxic products detrimental to the well and/or equipment. For example, sulfate reducing bacteria (SRB) produces hydrogen sulfide as a toxic and corrosive gas. Other types of microorganisms found in fluids include bacteria, yeast, viruses, algae, and the like.

For the reasons mentioned, attempts have been made to wash out, or chemically convert, the microorganisms within downhole fluids and/or within the subterranean reservoir. For example, sweeteners (e.g. nitrogen-containing hydrogen sulfide sweeteners) are available for removing sulfur species from a downhole fluid, but many of them have serious limitations. The amines released from the sweeteners when scavenging the sulfur species pose an overhead corrosion threat in various downstream processes, including distillation columns. Formaldehyde is a nitrogen-free sweetener, but it is also a potential carcinogen. Glyoxal is another nitrogen-free hydrogen sulfide sweetener, but its application is often limited due to its corrosivity and low boiling point. Metal oxides have also been proposed, but such applications are narrowed by the handling challenges and solid residual formation concerns to downstream refining catalysts and processes. Acrolein is a clean and extremely potent hydrogen sulfide/mercaptan sweetener, but it requires special handling due to toxicity concerns.

It would be desirable if methods were developed for decreasing an amount of microorganisms in fluids used or present in subterranean reservoir.

SUMMARY

There is provided, in one form, a method for decreasing microbial growth of at least one microorganism in a fluid by providing ultrasonic waves to the downhole fluid. Alternatively, the microbial growth may be prevented and/or inhibited; in yet another non-limiting embodiment, the microorganism(s) are sterilized within the fluid.

There is provided, in a non-limiting form, the fluid may be a downhole fluid. In addition to or alternative to, an effective amount of a gas may be provided to the fluid to further decrease the microbial growth by preventing and/or inhibiting the microbial growth.

There is further provided in an alternative non-limiting embodiment of the method that may include sonicating the ultrasonic waves into or to the downhole fluid with a sonication device. The downhole fluid may have a temperature ranging from about 25 C to about 100 C prior to and during the sonication. The downhole fluid may be or include drilling fluids, completion fluids, production fluids, injection fluids, stimulation fluids, refinery fluids, servicing fluids, and combinations thereof.

The ultrasonic waves, optional elevated temperature, and the optional gas provided to the fluid may decrease the microbial growth by preventing and/or inhibiting microbial growth.

DETAILED DESCRIPTION

It has been discovered that ultrasonic waves provided to a fluid may decrease microbial growth of at least one microbial population within a fluid. Ultrasonic waves have an oscillating sound pressure wave with a frequency greater than the upper limit of the human hearing range, i.e. above about 20 kilohertz (kHz). Ultrasonic waves may be produced and provided to employ a sonication technique and disrupt cellular membranes within a microorganism. The use of biocides and/or oxidizers may be decreased and/or eliminated when providing the ultrasonic waves to the fluid(s) as compared to an otherwise identical fluid or downhole fluid in the absence of the ultrasonic wave usage. 'Fluid' as used herein includes a 'still' fluid, i.e. a fluid resting in a tank, pipeline, etc.; a fluid stream, i.e. a fluid undergoing movement; and/or a fluid sample, i.e. a sample taken from a fluid.

When the ultrasonic waves are produced and provided to a fluid, this is typically referred to as sonication. The ultrasonic waves may agitate particles in a solution for mixing solutions, speeding a dissolution of a solid into a liquid, emulsifying a fluid, demulsifying a fluid, cell disruption of microorganisms within a fluid, fragmenting molecules of DNA of such microorganisms, dispersing nanoparticles in a fluid, and combinations thereof. The disruption of cell membranes within the microorganisms may be referred to as sonoporation, in a non-limiting instance, and may allow for release of cellular components. Fragmenting molecules of DNA shears the DNA into smaller fragments.

In a non-limiting embodiment, the ultrasonic waves may be provided to the fluid by a sonication device, such as but not limited to a Q500 Sonicator distributed by QSONICA, an LG SONIC e-line device, and the like. Regardless of the type of sonication device, it may have or include an ultrasonic processor, optional programmable features, optional digital display of operating parameters, may be optionally programmed and/or used from a remote location, and combinations thereof. The operating parameters may be or include adjustable pulsing of the intermittent producing and providing the ultrasonic waves, time periods for producing and providing the ultrasonic waves. In another non-limiting embodiment, the sonication device include a probe having a diameter ranging from about 0.1 millimeters (mm) to about 50 centimeters (cm). The probe may be removable and/or replaceable.

In another non-limiting embodiment, the ultrasonic waves may be produced and provided to the fluid from a transmitter or a plurality of transmitters. Employing a plurality of transmitters would allow the ultrasonic waves to be adjusted depending on the quality of the fluid at a particular location and at a particular point in time.

The ultrasonic waves produced and provided to the fluid may have a frequency greater than 20 kHz, alternatively from about 40 kHz independently to about 100 kHz, or from about 50 kHz independently to about 75 kHz in another non-limiting embodiment. The ultrasonic waves may be produced and provided for a period of at least three minutes, alternatively at least 12 minutes, at least 20 minutes in another non-limiting embodiment, or at least 30 minutes in yet another non-limiting embodiment. During the time duration, the sonication may be intermittently pulsed to start and stop at regular and/or irregular intervals. As used herein with respect to a range, "independently" means that any threshold may be used together with another threshold to give a suitable alternative range, e.g. about 40 kHz independently to about 50 kHz is also considered a suitable alternative range.

The microorganism(s) where the growth may be decreased by the ultrasonic waves may be or include a bacteria, a yeast, a virus, an algae, and combinations thereof. Non-limiting examples of the bacteria may be or include gram positive bacteria, gram negative bacteria, sulfate reducing bacteria, acid producing bacteria, nitrate reducing bacteria, cyanobacteria, and combinations thereof. Non-limiting examples of the yeast may be or include Ascomycotas, Basidiomycotas, Saccharomycetales, and combinations thereof. Non-limiting examples of the virus may be or include DNA viruses, RNA viruses, reverse transcribing viruses, and combinations thereof. Non-limiting examples of the algae may be or include Chromista, Rhizaria, Archaeplastida, and combinations thereof.

In a non-limiting embodiment, the fluid may be or include an oil-based fluid, a water-based fluid, and combinations thereof. Alternatively, the fluid may be a downhole fluid, such as but not limited to drilling fluids, completion fluids, production fluids, injection fluids, stimulation fluids, refinery fluids, servicing fluids, and combinations thereof. The fluid may have a temperature ranging from about 25 C independently to about 100 C, alternatively from about 40 C independently to about 80 C, or from about 50 C independently to about 70 C prior to and during the providing of the ultrasonic waves to the fluid. In a non-limiting embodiment, a heating element may be applied to the fluid to alter the temperature a pre-determined temperature.

In a non-limiting embodiment, an effective amount of at least one gas may be provided to the fluid (e.g. downhole fluid) at the same time or different time from the time of providing the ultrasonic waves to the fluid to further decrease the microbial growth. The gas(es) may produce free radicals within the fluid that may further decrease and/or sterilize the microbial populations, inhibit microbial growth, and a combination thereof. 'Decrease' as used herein with regards to the microbial growth includes slowing the growth of the microorganisms, completely stopping or preventing the growth of the microorganisms, sterilize the microorganisms, and combinations thereof.

Prevent or inhibit is defined herein to mean that the ultrasonic waves, optional heat pre-treatment to the fluid, and/or optional gas provided to the fluid may suppress or reduce the amount of microbial growth within the fluid if there are actually any microorganisms present within the fluid. That is, it is not necessary for microbial growth to be entirely prevented for the methods discussed herein to be considered effective, although complete prevention (i.e. sterilization) is a desirable goal.

The gas may be or include, but is not limited to, an inert gas, a noble gas, and combinations thereof. Non-limiting examples of the gas may be or include nitrogen (N2), argon, neon, helium, and combinations thereof. The effective amount of the gas(es) may range from 0.1 mg/L independently to about 100 mg/L, alternatively from about 10 mg/L independently to about 90 mg/L, or from about 25 mg/L independently to about 75 mg/L.

In a non-limiting embodiment, the producing and providing of the ultrasonic waves to the fluid may occur in a subterranean reservoir wellbore, a pipeline, a tank, a joint, or other connection or location within oilfield equipment and/or refinery equipment, and combinations thereof.

The invention will be further described with respect to the following Examples, which are not meant to limit the invention, but rather to further illustrate the various embodiments.

EXAMPLES

Example 1

A culture media of Luria-Bertani broth (LB) was inoculated with a sample of production water known to include sulfur-reducing bacteria. The biofilm was seen in the sample as sheet-like particles floating in the culture media. The sample was sonicated at 25 C, and after 12 seconds, the biofilm was completely disrupted. After 30 minutes, the cell culture was completely dispersed, and the culture media became transparent.

The sonication procedures for Examples 1-3 involved a QSONICA Q500 Sonicator with a ½ inch horn. The samples were sonicated at 20 kHz with a 70% amplitude for 1 minute cycles. After each cycle, the sample rested with no sonication for another 1 minute. Time intervals are reported as total time exposed to active sonication.

Example 2

A sonicated sample from Example 1 was plated on an LB agar media at various time intervals, i.e. $T_0$, $T_1$, $T_{12}$, $T_{21}$, and $T_{30}$ minutes. The samples were brought to 25 C and equilibrated at that temperature for at least one hour prior to sonication. The samples were then incubated at 37 C and held at this temperature overnight. The agar media from time intervals $T_0$, $T_1$, and $T_{12}$ minutes were heavily contaminated with bacteria. The agar media from time intervals $T_{21}$ and $T_{30}$ had no growth to suggest the samples at $T_{21}$ and $T_{30}$ were effectively sterilized.

Example 3

Two sonicated samples from Example 1 were plated on an LB agar media at time interval $T_{30}$ minutes. The samples were brought to 50 C and 60 C and equilibrated at their respective temperatures for at least one hour prior to sonication. The samples were then incubated at 37 C and held at this temperature overnight. Both of the agar media at 50 C and 60 C from time intervals $T_{30}$ were effectively sterilized. However, the elevated temperatures enhanced the sonication efficacy as compared to the same $T_{30}$ sample in Example 2. The samples were completely sterile after 3 minutes of sonication treatment when combined with the elevated temperatures.

In the foregoing specification, the invention has been described with reference to specific embodiments thereof, and has been described as effective in providing methods for decreasing microbial growth in a fluid. However, it will be evident that various modifications and changes can be made thereto without departing from the broader spirit or scope of the invention as set forth in the appended claims. Accordingly, the specification is to be regarded in an illustrative rather than a restrictive sense. For example, specific fluids, sonication devices, microorganisms, and the like falling within the claimed parameters, but not specifically identified or tried in a particular composition or method, are expected to be within the scope of this invention.

The present invention may suitably comprise, consist or consist essentially of the elements disclosed and may be practiced in the absence of an element not disclosed. For instance, the method for decreasing microbial growth in a downhole fluid may consist of or consist essentially of providing ultrasonic waves to the downhole fluid; and decreasing microbial growth of at least one microorganism in the downhole fluid.

The words "comprising" and "comprises" as used throughout the claims, are to be interpreted to mean "including but not limited to" and "includes but not limited to", respectively.

What is claimed is:

1. A method for decreasing microbial growth in a downhole fluid, wherein the method comprises:
   providing ultrasonic waves by a sonication device to the downhole fluid in a subterranean reservoir wellbore,
   agitating microorganism particles comprising at least one microorganism selected from the group consisting of a bacteria, a yeast, a virus, an algae, and combinations thereof. thereby
   decreasing microbial growth of the at least one microorganism in the downhole fluid by sonoporation,
   wherein the ultrasonic waves are provided at a frequency ranging from about 40 kHz to about 100 kHz.

2. The method of claim 1, wherein the at least one microorganism is selected from the group consisting of gram positive bacteria, gram negative bacteria, sulfate reducing bacteria, acid producing bacteria, nitrate reducing bacteria, and combinations thereof.

3. The method of claim 1, wherein the downhole fluid comprises a temperature ranging from about 25 C to about 100 C.

4. The method of claim 1, further comprising providing the downhole fluid with an effective amount of at least one gas at the same time or different time as providing the ultrasonic waves to the downhole fluid to further decrease microbial growth of the at least one microorganism in the fluid.

5. The method of claim 4, wherein the at least one gas is selected from the group consisting of an inert gas, a noble gas, and combinations thereof.

6. The method of claim 4, wherein the effective amount of the at least one gas ranges from about 0.1 mg/L to about 100 mg/L.

7. The method of claim 1, wherein the downhole fluid is an oil-based fluid, a water-based fluid, and combinations thereof.

8. The method of claim 1, wherein the downhole fluid is selected from the group consisting of drilling fluids, completion fluids, production fluids, injection fluids, stimulation fluids, refinery fluids, servicing fluids, and combinations thereof.

9. The method of claim 1, wherein the decreasing microbial growth comprises sterilizing the microbial growth of the at least one microorganism in the downhole fluid.

10. A method for decreasing microbial growth in a fluid, wherein the method comprises:
    providing ultrasonic waves by a sonication device to the fluid in a subterranean reservoir wellbore, wherein the ultrasonic waves are provided at a frequency ranging from about 40 kHz to about 100 kHz;
    agitating microorganism particles comprising at least one microorganism selected from the group consisting of a bacteria, a yeast, a virus, an algae, and combinations thereof;
    providing an effective amount of a gas to the fluid to thereby decrease an amount of at least one microorganism in the fluid; and
    decreasing microbial growth of an amount of at least one microorganism in the fluid by sonoporation.

11. The method of claim 10, wherein the fluid comprises a temperature ranging from about 25 C to about 100 C.

12. The method of claim 10, further comprising providing the fluid with an effective amount of at least one gas at the same time or different time as providing the ultrasonic waves to the fluid to further decrease microbial growth of the at least one microorganism in the fluid.

13. The method of claim 12, wherein the at least one gas is selected from the group consisting of an inert gas, a noble gas, and combinations thereof.

14. The method of claim 10, wherein the decreasing microbial growth comprises sterilizing the microbial growth of the at least one microorganism in the downhole fluid.

15. A method for decreasing microorganisms in a downhole fluid, wherein the method comprises:
    sonicating ultrasonic waves into the downhole fluid in a subterranean reservoir wellbore with a sonication device; wherein the ultrasonic waves are provided at a frequency ranging from about 40 kHz to about 100 kHz; wherein the downhole fluid comprises a temperature ranging from about 25 C to about 100 C;
    agitating microorganism particles comprising at least one microorganism selected from the group consisting of a bacteria, a yeast, a virus, an algae, and combinations thereof thereby
    decreasing microbial growth of an amount of at least one microorganism in the downhole fluid by sonoporation; and
    wherein the downhole fluid is selected from the group consisting of drilling fluids, completion fluids, production fluids, injection fluids, stimulation fluids, refinery fluids, servicing fluids, and combinations thereof.

* * * * *